(12) United States Patent
Tan et al.

(10) Patent No.: US 10,145,819 B2
(45) Date of Patent: Dec. 4, 2018

(54) METHOD FOR MEASURING THE PROPERTIES OF LIQUID BASED ON A QUARTZ CRYSTAL MICROBALANCE SENSOR

(71) Applicant: UNIVERSITY OF ELECTRONIC SCIENCE AND TECHNOLOGY OF CHINA, Chengdu, Sichuan (CN)

(72) Inventors: Feng Tan, Chengdu (CN); Duyu Qiu, Chengdu (CN); Peng Ye, Chengdu (CN); Hao Zeng, Chengdu (CN); Yong Zhao, Chengdu (CN); Jun Jiang, Chengdu (CN); Huiqing Pan, Chengdu (CN); Lianping Guo, Chengdu (CN); Shuhao Wu, Chengdu (CN)

(73) Assignee: UNIVERSITY OF ELECTRONIC SCIENCE AND TECHNOLOGY OF CHINA, Chengdu (CN)

(*) Notice: Subject to any disclaimer, the term of this patent is extended or adjusted under 35 U.S.C. 154(b) by 386 days.

(21) Appl. No.: 14/933,648

(22) Filed: Nov. 5, 2015

(65) Prior Publication Data

US 2016/0097743 A1 Apr. 7, 2016

(30) Foreign Application Priority Data

May 23, 2015 (CN) .......................... 2015 1 0198143

(51) Int. Cl.
*G01N 29/02* (2006.01)
*G01N 29/036* (2006.01)
*G01N 29/44* (2006.01)

(52) U.S. Cl.
CPC ......... *G01N 29/022* (2013.01); *G01N 29/036* (2013.01); *G01N 29/4436* (2013.01);
(Continued)

(58) Field of Classification Search
CPC ............... G01N 29/022; G01N 29/036; G01N 29/4436; G01N 2291/014; G01N 2291/02818; G01N 2291/0426
See application file for complete search history.

(56) References Cited

U.S. PATENT DOCUMENTS

| 5,201,215 A | 4/1993 | Granstaff et al. |
| 2004/0150428 A1* | 8/2004 | Itoh .................. G01N 27/126 327/1 |

(Continued)

OTHER PUBLICATIONS

Tan et al., "Separate density and viscosity measurements of unknown liquid using quartz crystal microbalance", AIP Advances 6, 095313 (2016).*

(Continued)

*Primary Examiner* — Mohamed Charioui
*Assistant Examiner* — Catherine Rastovski
(74) *Attorney, Agent, or Firm* — Oliff PLC

(57) ABSTRACT

The present invention provides a method for a method for measuring the properties of liquid based on a quartz crystal microbalance sensor, which employs two measurements to obtain two frequency shifts of the QCM sensor induced by two different volume of the sample liquid. The present invention creatively established the relationship between the density and viscosity of sample liquid and the frequency shifts of QCM sensor. With present invention, the density and viscosity of sample liquid can be obtained through two frequency shifts. Comparing to the conventional liquid property measurement. The measuring procedure of present invention are more simple, and the measuring results are more accurate. Moreover, the present invention consumes less volume of sample liquid, and has the features such as online, real time and quantitative.

2 Claims, 3 Drawing Sheets

(52) U.S. Cl.
CPC .............. *G01N 2291/014* (2013.01); *G01N 2291/02818* (2013.01); *G01N 2291/0426* (2013.01)

(56) References Cited

U.S. PATENT DOCUMENTS

| | | | | |
|---|---|---|---|---|
| 2009/0038859 A1* | 2/2009 | Itoh | ............... | G01N 5/02 177/25.13 |
| 2011/0061462 A1* | 3/2011 | Ichihashi | ............... | G01N 9/002 73/579 |
| 2011/0064514 A1* | 3/2011 | Merzon | ............... | A45C 3/02 402/74 |
| 2011/0309821 A1* | 12/2011 | Kondo | ............... | G01N 29/022 324/76.49 |

OTHER PUBLICATIONS

Itoh and Ichihashi, "Separate measurement of the density and viscosity of a liquid using a quartz crystal microbalance based on admittance analysis (QCM-A)", Meas. Sci. Technol. 22 015402 (2011).*

Ferrari et al., "In-Liquid Sensing of Chemical Compounds by QCM Sensors Coupled with High-Accuract ACC Oscillator", IEE Transactions on Instrumentation and Measurement, Jul. 2006.*

Kabazawa, K.K. et al.,"Frequency of a Quartz Microbalance in Contact with Liquid" Anal.Chem. 57 (1985) pp. 1770-1771.

Ward, Michael D. et al., "In Situ Interfacial Mass Detection with Piezoelectirc Transducers" Science, vol. 249 (1990) pp. 1000-1007.

Schumacher, Rolf "The Quartz Microbalance: A Novel Approach to the In-Situ Investigation of Interfacial Phenomena at the Solid/Liquid Junction," Angew. Chem. Int.Ed. Engl. vol. 29, No. 4 (Apr. 1990) pp. 329-343.

Hillman, A.R. et al., "Transport of Neutral Species in Electroactive Polymer Films," Chem. Soc.Faraday Trans. (1991) vol. 87, No. 13, pp. 2047-2053.

Martin, Stephen J. et al., "Characterization of a Quartz Crystal Mircobalance with Simultaneous Mass and Liquid Loading," Anal. Chem. (Oct. 15, 1991) vol. 63, No. 20, pp. 2272-2281.

Doy, N. et al. "Seperate Density and Viscosity Determination of Room Temperature Ionic Liquids using Dual Quartz Crystal Microbalances" (1990) pp. 287-290, iEEE Sensors.

Itoh, Atsushi et al., "Seperate measurement of the density and viscosity of a liquid using a quartz crystal microbalance based on admittance analysis (QCM-A)" Meas. Sci. and Technol. 22 (2011) 01540, pp. 1-6.

* cited by examiner

METHOD FOR MEASURING THE PROPERTIES OF LIQUID BASED ON A QUARTZ CRYSTAL MICROBALANCE SENSOR

FIELD OF THE INVENTION

This application claims priority under the Paris Convention to Chinese Patent Application No. 201510198143.2, Filed Apr. 23, 2015, the entirety of which is hereby incorporated by reference for all purposes as if fully set forth herein.

The present invention relates to the field of electronic measurement technology, more particularly to a method for measuring the properties of liquid based on a quartz crystal microbalance (QCM) sensor, the properties of liquid comprise density and viscosity, the method can be applied to chemistry, materials, biology, physics, and so forth.

BACKGROUND OF THE INVENTION

The Ionic liquids are widely used in various applications with ever growing interest. However, for millions of potentially available ionic liquids, the properties of a few percentages of them have been measured. Meanwhile, the majority of the samples to be analyzed in the fields of analytical chemistry and biomedical science are within liquid environment. Therefore, the analysis of liquid must be performed. When measuring the properties of liquid, we usually give attention to its density and viscosity.

In prior art, when measuring the density and viscosity of liquid, an analytical electronic balance and a viscometer are used separately. First, the mass of the liquid is weighed by an analytical electronic balance, and the density of liquid can be obtained according to the formula (1):

$$\rho_l = \frac{m_l}{V_l}; \qquad (1)$$

Then, the viscosity of liquid is measured by a viscometer, such as rotary viscometer, ultrasonic viscometer and capillary viscometer. The conventional method mentioned above has certain limitations and deficiencies for analytical chemistry and biomedical field, which are mainly as follows:

(1). The accuracy of currently available analytical electronic balances can only reach the magnitude of microgram, while the higher accuracy is pursued in analytical chemistry and biomedical field;

(2). In analytical chemistry and biomedical field, usually, the price of sample is extremely expensive, while the conventional method requires a relatively large amount of sample;

(3). The conventional method cannot provide the analysis results online and real time.

The method for measuring the properties of liquid based on quartz crystal microbalance sensor can compensate for the mentioned deficiencies to a certain extent. Thereby the application of quartz crystal microbalance sensor has become a research focus in liquid property measurement.

The pressure sensor based on quartz crystal microbalance has been commercialized, and widely applied in biology, chemistry, physics and other fields. However, only few researches relate to the liquid property measuring with quartz crystal microbalance.

So far, only a few papers concerning the method for measuring the density and viscosity of an unknown solution based on QCM sensor have been published, and certain limitations and deficiencies still exist. K. Kanazawa, J. G. Gordon et al. proved that the frequency shift of a QCM sensor and the property of the contacted liquid, i.e. the product of the density and viscosity, exist certain relationship (K. K. Kanazawa, J. G. Gordon, Frequency of a quartz microbalance in contact with liquid, Anal. Chem. 57 (1985) 1770-1771). However, they ignored the fact that the mass of liquid can cause frequency shift of the QCM sensor as well. Ward, M. D and Buttry, D. A et al. published "In situ interfacial mass detection with piezoelectric transducers, Science 1990, 249, 1000-1007" in Science in 1990, they reported that the mass of liquid on the surface of the QCM sensor can also shift the frequency. After that, Schumacher group and A. R. Loveday group verified the validity of the conclusion (R. Schumacher, The Quartz Microbalance: A Novel Approach to the In-Situ Investigation of Interfacial Phenomena at the Solid/Liquid Junction, Chem. Int. Ed. Engl. 1990, 29, 329-343; Hillman, A. R.; Loveday, D. C.; Swam, M. J. J. Transport of neutral species in electroactive polymer films, Chem. Soc. Faraday Trans. 1991, 87, 2047-2053). Later, Martin et al. added liquid mass effect to the frequency shift of the QCM sensor in liquid phase applications. (Stephen J. Martin, Victoria Edwards Granstaff, and Gregory C. Frye, Characterization of a Quartz Crystal Microbalance with Simultaneous Mass and Liquid Loading, Anal. Chem. 1091, 63, 2272-2281).

Martin and coworkers report a continuum model that describes the QCM simultaneously loaded by a thin surface mass layer and a semi infinite Newtonian liquid ("Stephen J. Martin, Victoria Edwards Granstaff, and Gregory C. Frye, Characterization of a Quartz Crystal Microbalance with Simultaneous Mass and Liquid Loading, Anal. Chem. 1091, 63, 2272-2281"), but they think that with only one QCM sensor, the density and viscosity of liquid cannot be extracted. With such assumption, they invented a measurement method with dual QCM sensors and applied for a patent (Patent No. US005201215A) in 1991. In that method, one QCM sensor is with a smooth surface which only responses to the product of liquid density and viscosity, while the other QCM sensor is with textured surface which not only response to the product of liquid density and viscosity but also an additional response to the liquid density. In 2009, N. Doy, G. McHale and M. I. Newton et al. made further research based on the previous work of Martin. They put forward the explicit expression of liquid density and viscosity based on the dual QCM sensors measurement method ("Separate Density and Viscosity Determination of Room Temperature Ionic Liquids using Dual Quartz Crystal Microbalances").

The two methods mentioned above all adopt two different QCM sensors, thus leading to a more complex process and less accurate results.

In 2011, Atsushi Itoh and Motoko Ichihashi et al. simultaneously measured the frequency shift and the conductance shift of QCM sensor, and established equations to obtain the density and viscosity of liquid (Atsushi Itoh and Motoko Ichihashi, Separate measurement of the density and viscosity of a liquid using a quartz crystal microbalance based on admittance analysis (QCM-A), Meas. Sci. Technol. 22(2011)015402). Although only single QCM sensor is used, the measurement process is more complex and the accuracy of the result needs to be improved, and moreover, they did not gave the explicit expression of liquid density and viscosity.

SUMMARY OF THE INVENTION

The present invention aims to overcome the deficiencies of prior art and provides a method for measuring the properties of liquid based on a quartz crystal microbalance sensor to obtain the density and viscosity of liquid, simplify the measuring process, and improve the accuracy of the measurement.

To achieve these objectives, in accordance with the present invention, a method for measuring the properties of liquid based on a quartz crystal microbalance sensor is provided, comprising the following steps:

(1). connecting a QCM sensor with smooth surface to a driving circuit, where the driving circuit is connected to a DC power, and the output of the driving circuit is connected to a frequency counter;

recording the counting value displayed on the frequency counter, after the DC power is powered on, and the QCM sensor begins to work, where the counting value is the reference resonant frequency $f_o$ of the QCM sensor;

(2). loading a certain amount of sample liquid onto the QCM sensor's surface, where the volume of the sample liquid is $V_{L1}$, and then, recording the counting value displayed on the frequency counter, where the counting value is the first resonant frequency $f_1$ of the QCM sensor, and the first frequency shift is $\Delta f_1 = f_1 - f_0$;

(3). based on step (2), loading another certain amount of sample liquid onto the QCM sensor's surface, where the volume of the sample liquid is $V_{L2}$, and then, recording the counting value displayed on the frequency counter, where the counting value is the second resonant frequency $f_2$ of the QCM sensor, and the second frequency shift is $\Delta f_2 = f_2 - f_0$;

when the volume of sample liquid varies from $V_{L1}$ to $V_{L2}$, the difference between the second frequency shift and the first frequency shift of the QCM sensor is $\Delta f_2 - \Delta f_1$.

(4) the density of sample liquid $\rho_L$ is calculated:

$$\rho_L = \frac{\Delta f_2 - \Delta f_1}{K_{Pf} \cdot C_{Pf} \cdot V_{L2} \cdot f_0};$$

where $C_{Pf}$ is a pressure-frequency constant, $K_{Pf}$ is the pressure sensitivity coefficient of the QCM sensor, and obtained as follow:

$$K_{Pf} = f_0 \cdot K_f / nD;$$

where n is the overtone number of the QCM sensor, D is the diameter of the QCM sensor's electrode, $K_f$ is the force-frequency constant of the QCM sensor;

(5). the viscosity of sample liquid $\eta_L$ is calculated:

$$\eta_L = \frac{K_{Pf} \cdot C_{Pf}}{(\Delta f_2 - \Delta f_1) \cdot V_{L2} \cdot f_0} \cdot \left[ \frac{\Delta f_1 \cdot V_{L2} - V_{L1} \cdot (\Delta f_2 - \Delta f_1)}{K_{Tf} \cdot C_{Lf}} \right]^2;$$

where $K_{Tf}$ is the stress sensitivity coefficient of the QCM sensor, $C_{Lf}$ is the stress-frequency coefficient of the QCM sensor, and $C_{Lf}$ is related to the properties of the sample liquid.

The objectives of the present invention are realized as follows:

The present invention, i.e. method for measuring the properties of liquid based on a quartz crystal microbalance sensor employs two measurements to obtain two frequency shifts of the QCM sensor induced by two different volume of the sample liquid. The present invention creatively established the relationship between the density and viscosity of sample liquid and the frequency shifts of QCM sensor. With present invention, the density and viscosity of sample liquid can be obtained through two frequency shifts.

Comparing to the conventional liquid property measurement, the present invention is able to obtain the density and viscosity of sample liquid through the above mentioned equations by applying two frequency shifts of a single QCM sensor induced by two different volume of the sample liquid. Therefore, the measuring procedure are more simple, and the measuring results are more accurate. Moreover, the present invention consumes less volume of sample liquid, and has the features such as online, real time and quantitative.

BRIEF DESCRIPTION OF THE DRAWING

The above and other objectives, features and advantages of the present invention will be more apparent from the following detailed description taken in conjunction with the accompanying drawings, in which.

DETAILED DESCRIPTION OF THE PREFERRED EMBODIMENT

Figures 1A, 1B:
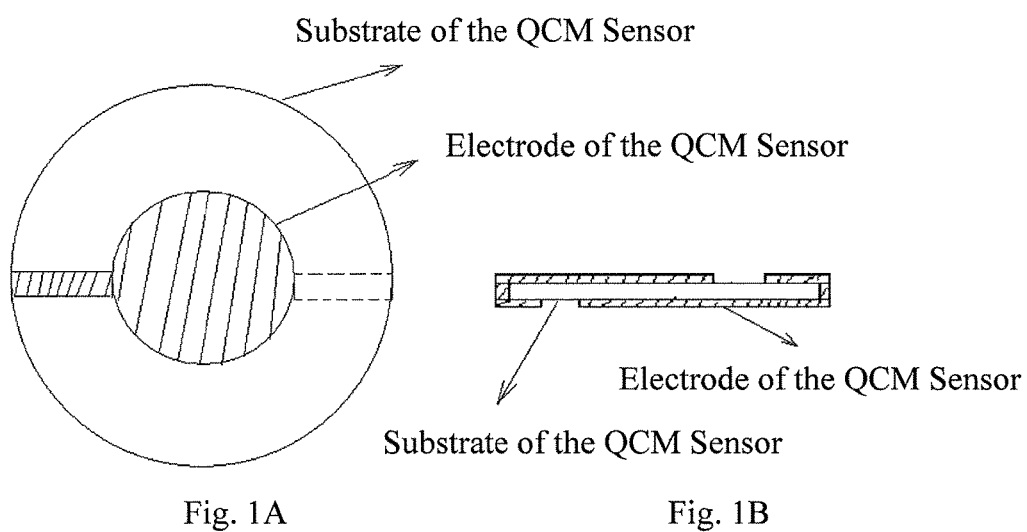
FIGS. 1A and 1B are diagrams representing a typical structure of a QCM sensor, where (A) is the positive side, (B) is the cross section.

Hereinafter, preferred embodiments of the present invention will be described with reference to the accompanying drawings. It should be noted that the similar modules are designated by similar reference numerals although they are illustrated in different drawings. Also, in the following description, a detailed description of known functions and configurations incorporated herein will be omitted when it may obscure the subject matter of the present invention.

QCM sensor is a kind of device which is able to convert the stress or pressure on its surface into frequency by piezoelectric effect. As shown in FIG. 1, the typical structure of a QCM sensor is a piezoelectric crystal sensor which is sandwiched between two electrodes.

When sample liquid is loaded onto the surface of a QCM sensor, the QCM sensor is subject to pressure and stress at the same time, which frequency response is:

$$f = K_{Pf} \cdot P \cdot f_0 + K_{Tf} \cdot T \cdot f_0 \quad (2)$$

where $K_{Pf}$ is the pressure sensitivity coefficient of the QCM sensor and the coefficient $K_{Pf} = f_0 \cdot K_f / nD$, P is the pressure exerted onto the QCM sensor's surface by sample liquid, $f_0$ is the natural reference frequency, i.e. the reference resonant frequency of the QCM sensor, $K_{Tf}$ is the stress sensitivity coefficient of the sensor, T is the stress exerted onto the QCM sensor's surface by sample liquid, n is the overtone number, D is the diameter of the QCM sensor's electrode, $K_f$ is the force-frequency constant of the QCM sensor.

When the QCM sensor works in air or vacuum circumstance, and the QCM sensor's surface does not adsorb medium, the surface stress of the QCM sensor does not change. Meanwhile, the frequency shift of the QCM sensor only results from the surface pressure change. Therefore, the related companies and manufacturers designed and produced the piezoelectric bulk acoustic resonant pressure sensor. At present this kind of sensor is mainly made of ceramic or quartz crystal. If the QCM sensor's surface adsorbs medium, the surface stress and pressure of the QCM sensor will change. The frequency shift of the QCM sensor caused by surface stress change and pressure change is:

$$\Delta f = K_{Pf} \cdot \Delta P \cdot f_0 + K_{Tf} \cdot \Delta T \cdot f_0 \qquad (3).$$

When sample liquid is loaded onto the QCM sensor's surface, the pressure and properties of sample liquid can cause a frequency shift, the stress variation $\Delta T$ caused by the liquid properties is:

$$\Delta T = C_{Lf} \sqrt{\rho_L \cdot \eta_L} \qquad (4);$$

where $C_{Lf}$ is the stress-frequency coefficient of the QCM sensor, and $C_{Lf}$ is related to liquid properties, $\rho_L$ is the density of sample liquid, $\eta_L$ is the viscosity of sample liquid.

Obviously, for a given sample liquid, its viscosity and density are determined at somewhat of temperature, thus the stress variation of the QCM sensor induced by the properties of sample liquid is determinate, and the frequency shift induced by the properties of sample liquid is also determined. That is to say, once sample liquid is fixed, $K_{Tf} \cdot \Delta T \cdot f_0$ will be a constant. Then the frequency shift of QCM sensor is only related to the pressure induced by sample liquid which is loaded onto the QCM sensor's surface, the pressure variation $\Delta P$ caused by sample liquid is:

$$\Delta P = C_{Pf} \rho_L \cdot V_L \qquad (5);$$

where $C_{Pf}$ is the pressure frequency coefficient, $\rho_L$ is the liquid density, $V_L$ is the volume of sample liquid loaded onto the QCM sensor's surface.

When the $V_{L1}$ of sample liquid is loaded onto the QCM sensor's surface, the first frequency shift results from the mutual effects of the surface pressure and the properties of sample liquid. the first frequency shift $\Delta f_1$ can be calculated from the following formula:

$$\Delta f_1 = K_{Pf} \cdot C_{Pf} \rho_L \cdot V_{L1} \cdot f_0 + K_{Tf} \cdot C_{Lf} \sqrt{\rho_L \cdot \eta_L \cdot f_0} \qquad (6).$$

When the $V_{L2}$ of sample liquid is added onto the QCM sensor's surface, the second frequency shift results from the mutual effects of the combined surface pressure and the properties of sample liquid. the second frequency shift $\Delta f_2$ can be calculated from the following formula:

$$\Delta f_2 = K_{Pf} \cdot C_{Pf} \rho_L \cdot (V_{L1} + V_{L2}) \cdot f_0 + K_{Tf} \cdot C_{Lf} \sqrt{\rho_L \cdot \eta_L \cdot f_0} \qquad (7).$$

The difference between the second frequency shift and the first frequency shift is:

$$\Delta f_2 - \Delta f_1 = K_{Pf} \cdot C_{Pf} \rho_L \cdot V_{L2} \cdot f_0 \qquad (8).$$

The density of sample liquid $\rho_L$ can be calculated according to the formula (8), which can be expressed as:

$$\rho_L = \frac{\Delta f_2 - \Delta f_1}{K_{Pf} \cdot C_{Pf} \cdot V_{L2} \cdot f_0}. \qquad (9)$$

Substituting formula (9) into formula (6), the viscosity of liquid $\eta_L$ can be obtained as:

$$\eta_L = \frac{K_{Pf} \cdot C_{Pf}}{(\Delta f_2 - \Delta f_1) \cdot f_0 \cdot V_{L2}} \cdot \left[ \frac{\Delta f_1 \cdot V_{L2} - V_{L1} \cdot (\Delta f_2 - \Delta f_1)}{K_{Tf} \cdot C_{Lf}} \right]^2. \qquad (10)$$

where $\Delta f_1$ and $\Delta f_2$ are frequency shift caused by the $V_{L1}$ and $V_{L2}$ of sample liquid respectively; $K_{Pf}$ is the pressure sensitivity coefficient of the QCM sensor, $K_{Tf}$ is the stress sensitivity coefficient of the QCM sensor, $C_{Pf}$ is the pressure-frequency coefficient, $C_{Lf}$ is the stress-frequency coefficient of the QCM sensor, and $C_{Lf}$ is related to the properties of the sample liquid, and $f_0$ is the natural (reference) resonant frequency of the QCM sensor, $\rho_L$ and $\eta_L$ are the density and viscosity of the sample liquid respectively.

The present invention, i.e. method method for measuring the properties of liquid based on a quartz crystal microbalance sensor can be realized according to formula (9) and formula (10).

The present invention converts the density and viscosity of the sample liquid into the corresponding frequency shift, and calculates them according to two frequency shifts, which are obtained by measuring the resonant frequency of the QCM sensor twice, when different volume of sample liquid is loaded onto the QCM sensor's surface.

Figure 2:
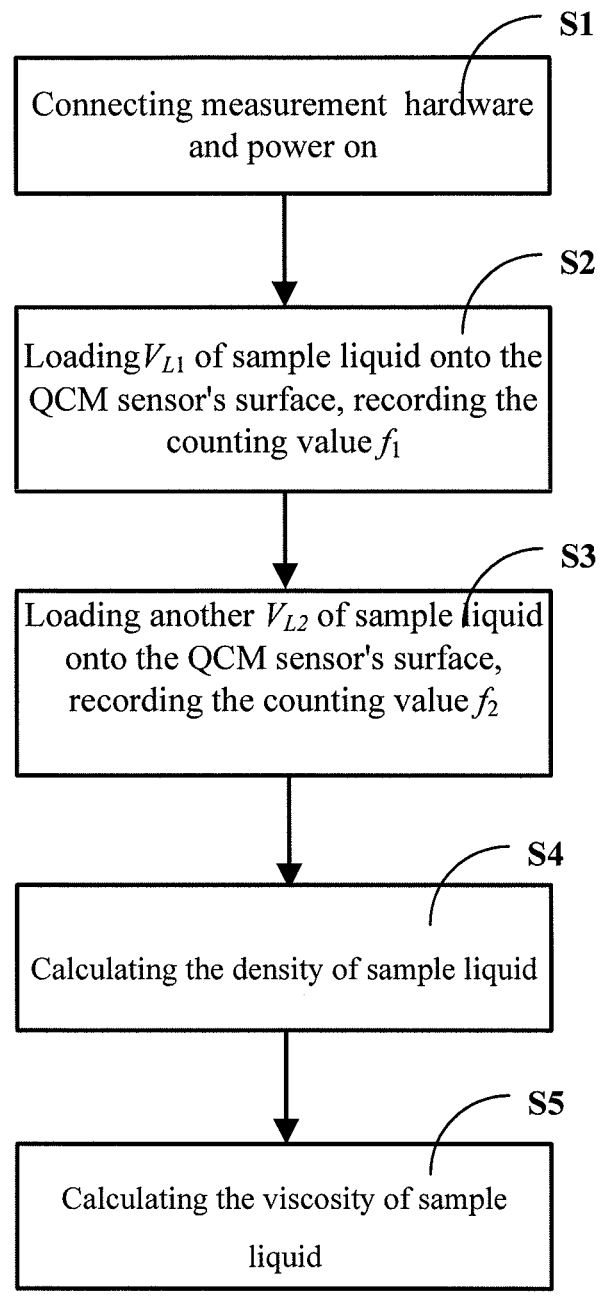
FIG. 2 is a flow chart diagram of liquid properties measurement based on a QCM sensor in accordance with the present invention.
Figure 3:
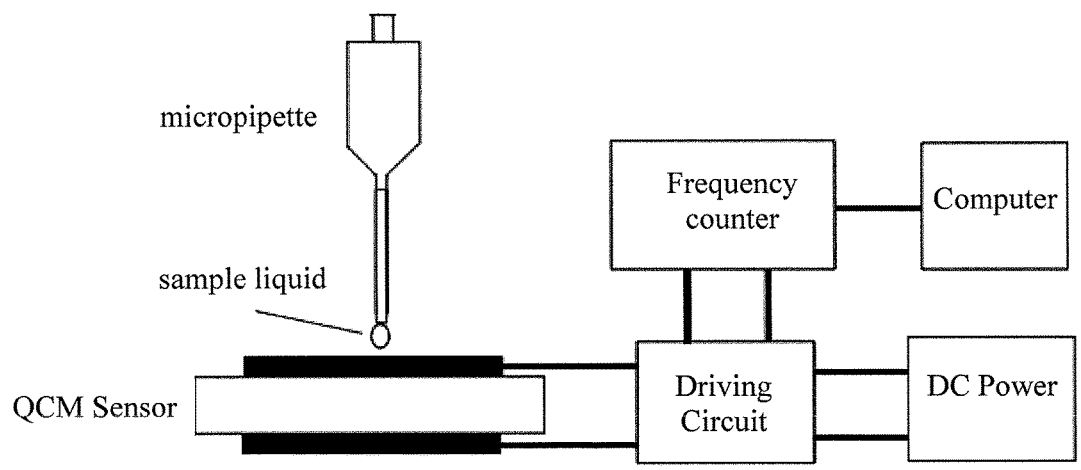
FIG. 3 is a functional block diagram of liquid properties measurement based on a QCM sensor in accordance with the present invention.

When implementing the present invention, only one QCM sensor is needed, and only small amount of sample liquid at the order of μL magnitude is loaded onto the QCM sensor's surface. With recording the resonant frequency of the QCM sensor twice, when different volume of sample liquid is loaded onto the QCM sensor's surface, the density and viscosity of the sample liquid can be obtained by formula (9) and (10). As shown in FIG. 2, the present invention can be implemented by the following steps:

Step S1: connecting a QCM sensor to a driving circuit, where the driving circuit is connected to a DC power, the output of the driving circuit is connected to a frequency counter, and the computer is connected to the frequency to record the counting value, the detailed connection is shown in FIG. 3;

recording the counting value displayed on the frequency counter, after the DC power is powered on, and the QCM sensor begins to work, where the counting value is the reference resonant frequency $f_0$ of the QCM sensor;

Step S2: loading a certain amount of sample liquid onto the QCM sensor's surface via a micropipette, where the volume of the sample liquid is $V_{L1}$, and then, recording the counting value displayed on the frequency counter; the counting value is the first resonant frequency $f_1$ of the QCM sensor, and the first frequency shift is $\Delta f_1 = f_1 - f_0$;

Step S3: based on Step S2, loading another certain amount of sample liquid onto the QCM sensor's surface via the micropipette, where the volume of the sample liquid is $V_{L2}$, and then, recording the counting value displayed on the frequency counter, where the counting value is the second resonant frequency $f_2$ of the QCM sensor, and the second frequency shift is $\Delta f_2 = f_2 - f_0$;

Step S4: on the basis of Step S2 and S3, it is apparent that when the volume of sample liquid varies from $V_{L1}$ to $V_{L2}$, the difference between the second frequency shift and the first frequency shift of the QCM sensor is $\Delta f_2 - \Delta f_1$, the density of sample liquid can be obtained from the formula (9);

Step S5: on the basis of Step S2, S3 and S4, the viscosity of sample liquid can be obtained from the formula (10).

The essence of the present invention is that both the liquid pressure and the properties of liquid can cause the QCM sensor a frequency shift, when sample liquid is loaded onto the QCM sensor's surface. Moreover, once the sample liquid is fixed, the viscosity and density of sample liquid are determinate. The stress variation of the QCM sensor induced by the properties of the sample liquid is determinate, and the frequency shift induced by the properties of the sample liquid is a constant at a given temperature. When another certain amount of sample liquid is loaded onto the QCM sensor's surface, the frequency shift of the QCM sensor is only related to the mass of sample liquid. Deducting the frequency shift caused by the properties of sample liquid and using the relationship between the pressure change and the frequency shift, the density of sample liquid can be obtained. On the basis of the density of sample liquid, the viscosity of sample liquid is obtained.

The present invention has many advantages, such as saving reagent and time, wide of response spectrum, simplicity of operation, real-time output, and quantitative analysis. Comparing to conventional measurements of the density and viscosity, The present invention creatively established the relationship between the density and viscosity of sample liquid and the frequency shifts of QCM sensor. With the present invention, the density and viscosity of sample liquid can be obtained with the variation of frequency shift. Comparing to conventional methods, the present invention is able to obtain the density and viscosity of sample liquid with the described algorithm, i.e. formula (9) and (10) by applying two frequency shifts of a single QCM sensor induced by two different volume of the sample liquid. Moreover, the measuring processes are greatly simplified, the complexity of measurement system is significantly reduced, and the measurement accuracy is also enhanced.

EXAMPLE

As shown in FIG. 3, a QCM sensor with 10 MHz of reference resonant frequency is chosen in the measurement system.

Step1: Connecting the QCM sensor with smooth surface to a driving circuit. The driving circuit is connected to a DC power. The output of the driving circuit is connected to a frequency counter. After the DC power is turned on, the QCM sensor begins to work. The reference resonant frequency $f_0$=10.00000 MHz is recorded.

Step2: loading a certain amount of sample liquid onto the QCM sensor's surface, then recording the counting value displayed on the frequency counter, thus the first resonant frequency $f_1$ of the QCM sensor is obtained. In the example, the first resonant frequency $f_1$ is 9.999620 Hz, the volume of the sample liquid $V_{L1}$ is 4 μL, and the first frequency shift $\Delta f_1$ is −380 Hz.

Step3: based on Step2, loading another certain amount of sample liquid onto the QCM sensor's surface, then recording the counting value displayed on the frequency counter, thus the second resonant frequency $f_2$ of the QCM sensor is obtained. In the example, the second resonant frequency $f_2$ is 9.999597 Hz, the volume of the sample liquid $V_{L2}$ is 6 μL, and the second frequency shift $\Delta f_2$ is −403 Hz.

Step4: the difference between the second frequency shift and the first frequency shift of the QCM sensor is $\Delta f_2 - \Delta f_1$=−23 Hz.

Step5: Substituting $C_{Pf}$=7.3903×10$^4$ m·Hz$^2$, $K_{Pf}$=−23.3×10$^{-15}$ (msN$^{-1}$), $K_{Tf}$=−2.75×10$^{-11}$ (m$^2$/N), $C_{Lf}$=−1.2877×10$^6$ m·$\sqrt{Hz^3}$ into formula (9) and formula (10), The density $\rho_1$=1.0 g/cm$^3$ and viscosity $\eta_1$=0.894 mPa·s of sample liquid can be obtained.

Repeating the above steps, the density and viscosity of NaCl, KCl, HCl solutions with different concentrations of 10%, 20%, 30% can be obtained and shown in table 1 (25±2° C.).

TABLE 1

| | Solution | | | | | | | | |
|---|---|---|---|---|---|---|---|---|---|
| | NaCl | | | KCl | | | HCl | | |
| | Concentration (wt %) | | | | | | | | |
| | 10 | 20 | 30 | 10 | 20 | 30 | 10 | 20 | 30 |
| Density (g/cm$^3$) | 1.068 | 1.156 | 1.22 | 1.28 | 1.40 | 1.51 | 0.97 | 1.01 | 1.11 |
| Viscosity (mPa·s) | 1.1 | 1.7 | 1.9 | 0.86 | 0.90 | 0.98 | 1.5 | 1.6 | 2.4 |

Obviously, the present invention do not confined to the above embodiments or other equivalents, QCM sensor can be any of piezoelectric resonant sensor made of piezoelectric materials, such as piezoelectric ceramics, piezoelectric films, quartz crystal, LiTaO3 crystal, and the shape of QCM sensor can be circle, rectangle or ellipse.

While illustrative embodiments of the invention have been described above, it is, of course, understand that various modifications will be apparent to those of ordinary skill in the art. Such modifications are within the spirit and scope of the invention, which is limited and defined only by the appended claims.

What is claimed is:

1. A method for measuring the properties of a liquid based on a quartz crystal microbalance (QCM) sensor, the method comprising:

connecting the QCM sensor to a driving circuit, the driving circuit being connected to a direct current (DC) power supply, and the output of the driving circuit being connected to a frequency counter;

recording a first counting value displayed on the frequency counter, after the DC power supply is powered on, and the QCM sensor begins to work, the first counting value being a reference resonant frequency $f_0$ of the QCM sensor;

after a certain amount of a sample liquid has been loaded onto the QCM sensor's surface, where a volume of the sample liquid is $V_{L1}$, recording a second counting value displayed on the frequency counter, where the second counting value is a first resonant frequency $f_1$ of the QCM sensor, and a first frequency shift is $\Delta f_1 = f_1 - f_0$;

after another certain amount of the sample liquid is loaded onto the QCM sensor's surface, where a volume of the sample liquid is $V_{L2}$, recording a third counting value displayed on the frequency counter, the third counting value being the second resonant frequency $f_2$ of the QCM sensor, and the second frequency shift being $\Delta f_2 = f_2 - f_0$;

when the volume of the sample liquid varies from $V_{L1}$ to $V_{L2}$, a difference between the second frequency shift and the first frequency shift of the QCM sensor is $\Delta f_2 - \Delta f_1$;

calculating a density of the sample liquid $\rho_L$ based on the formula:

$$\rho_L = \frac{\Delta f_2 - \Delta f_1}{K_{Pf} \cdot C_{Pf} \cdot V_{L2} \cdot f_0},$$

where $C_{Pf}$ is a pressure-frequency constant, $K_{Pf}$ is the pressure sensitivity coefficient of the QCM sensor, which is obtained based on the following formula: $K_{Pf} = f_0 \cdot K_f / nD$, where n is an overtone number of the QCM sensor's electrode, D is a diameter of the QCM sensor's electrode, $K_f$ is a force-frequency constant of the QCM sensor; and calculating the viscosity of the sample liquid $\eta_L$ based on the following formula:

$$\eta_L = \frac{K_{Pf} \cdot C_{Pf}}{(\Delta f_2 - \Delta f_1) \cdot V_{L2} \cdot f_0} \cdot \left[ \frac{\Delta f_1 \cdot V_{L2} - V_{L1} \cdot (\Delta f_2 - \Delta f_1)}{K_{Tf} \cdot C_{Lf}} \right]^2,$$

where $K_{Tf}$ is a stress sensitivity coefficient of the QCM sensor, $C_{Lf}$ is a stress-frequency coefficient of the QCM sensor, and $C_{Lf}$ is related to the properties of the sample liquid.

2. A method comprising:

after a direct current (DC) power supply is powered on, and a quartz crystal microbalance (QCM) sensor begins to work: recording a first counting value displayed on a frequency counter, the first counting value being a reference resonant frequency of the QCM sensor, the QCM sensor being connected to a driving circuit, the driving circuit being connected to a direct current (DC) power supply, and the output of the driving circuit being connected to the frequency counter;

after a certain amount of a sample liquid has been loaded onto the QCM sensor's surface, where a volume of the sample liquid is $V_{L1}$, recording a second counting value displayed on the frequency counter; the second counting value being a first resonant frequency of the QCM sensor;

after another certain amount of the sample liquid is loaded onto the QCM sensor's surface, where a volume of the sample liquid is $V_{L2}$, recording a third counting value displayed on the frequency counter, the third counting value being a second resonant frequency of the QCM sensor;

when the volume of the sample liquid varies from $V_{L1}$ to $V_{L2}$, calculating a density of the sample liquid based on a pressure-frequency constant, and a pressure sensitivity coefficient of the QCM sensor;

and calculating a viscosity of the sample liquid based on a stress sensitivity coefficient of the QCM sensor; and a stress-frequency coefficient of the QCM sensor.

* * * * *